(12) United States Patent
Turnbull et al.

(10) Patent No.: US 9,247,890 B2
(45) Date of Patent: Feb. 2, 2016

(54) EXPERT SYSTEM TO FACILITATE SOURCE LOCALIZATION OF BRAIN ELECTRICAL ACTIVITY

(71) Applicant: Case Western Reserve University, Cleveland, OH (US)

(72) Inventors: John Turnbull, Westlake, OH (US); Mehdi Hamaneh, Shaker Heights, OH (US); Farhad Kaffashi, Cleveland Heights, OH (US); Hans Luders, Chagrin Falls, OH (US); Ken Loparo, Chesterland, OH (US); Samden Lhatoo, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 442 days.

(21) Appl. No.: 13/665,323

(22) Filed: Oct. 31, 2012

(65) Prior Publication Data

US 2013/0109996 A1  May 2, 2013

Related U.S. Application Data

(60) Provisional application No. 61/553,688, filed on Oct. 31, 2011.

(51) Int. Cl.
*A61B 5/04* (2006.01)
*A61B 5/0476* (2006.01)
*A61B 5/00* (2006.01)

(52) U.S. Cl.
CPC .......... *A61B 5/04012* (2013.01); *A61B 5/0476* (2013.01); *A61B 5/4094* (2013.01); *A61B 5/7203* (2013.01); *A61B 5/7264* (2013.01); *A61B 5/0035* (2013.01); *A61B 5/0042* (2013.01); *A61B 5/726* (2013.01); *A61B 5/743* (2013.01); *A61B 5/7425* (2013.01)

(58) Field of Classification Search
USPC .......................................... 600/544
See application file for complete search history.

(56) References Cited

U.S. PATENT DOCUMENTS

| 6,330,470 | B1 * | 12/2001 | Tucker et al. | 600/544 |
| 2005/0027205 | A1 * | 2/2005 | Tarassenko et al. | 600/529 |
| 2005/0115561 | A1 * | 6/2005 | Stahmann et al. | 128/200.24 |
| 2006/0270920 | A1 * | 11/2006 | Al-Ali et al. | 600/323 |

FOREIGN PATENT DOCUMENTS

WO  WO 2011058059 A1 *  5/2011

OTHER PUBLICATIONS

Krings et al. Accuracy of EEG dipole source localization using implanted sources in the human brain. Clinical Neurophysiology 110 (1999) 106-114.*

* cited by examiner

*Primary Examiner* — Etsub Berhanu
(74) *Attorney, Agent, or Firm* — Tarolli, Sundheim, Covell & Tummino LLP

(57) ABSTRACT

A system or method can facilitate source localization of brain electrical activity. In one example, an expert system can be utilized to evaluate the source localization results and, based on the acceptability of the results, adjust a data preparation phase to provide for acceptable source localization.

18 Claims, 12 Drawing Sheets

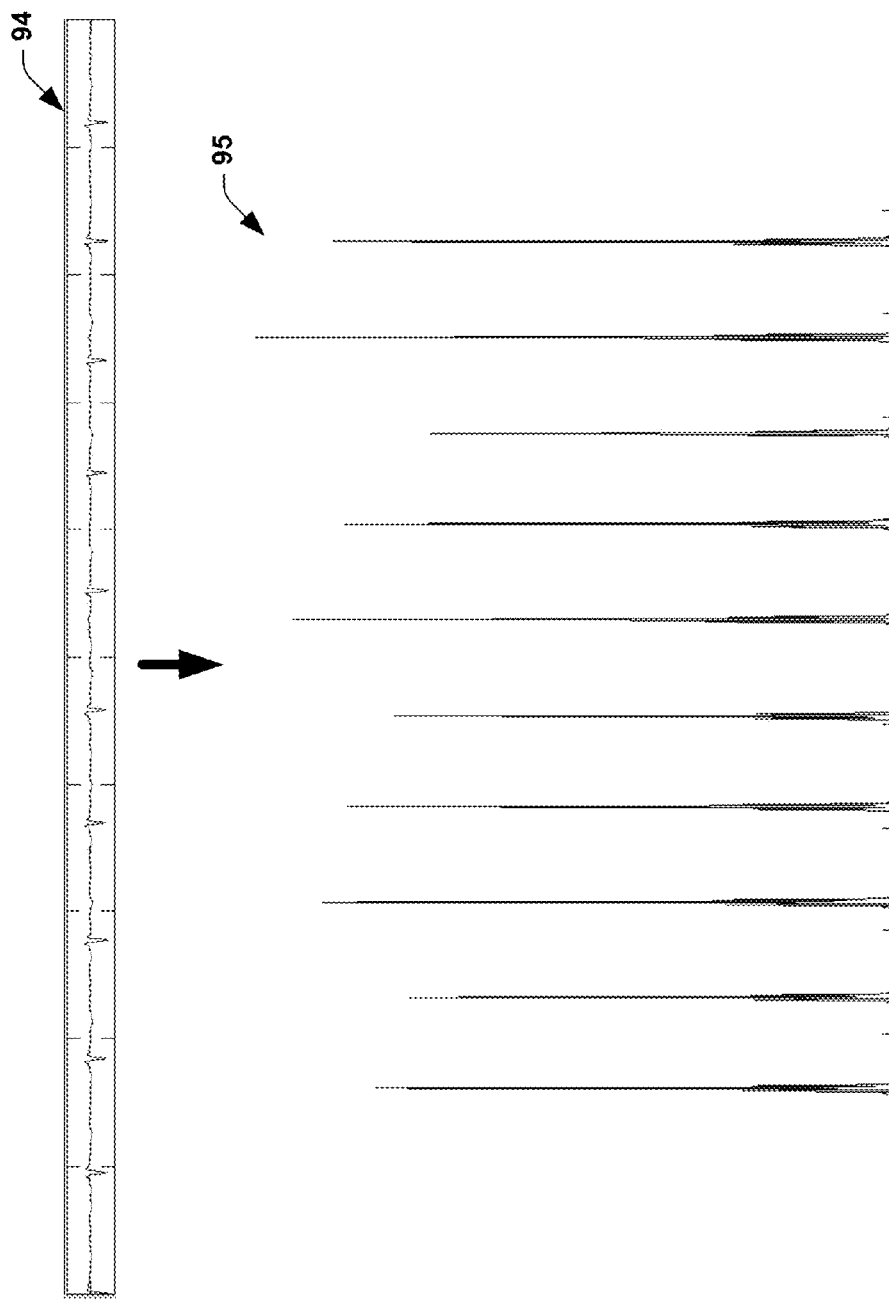

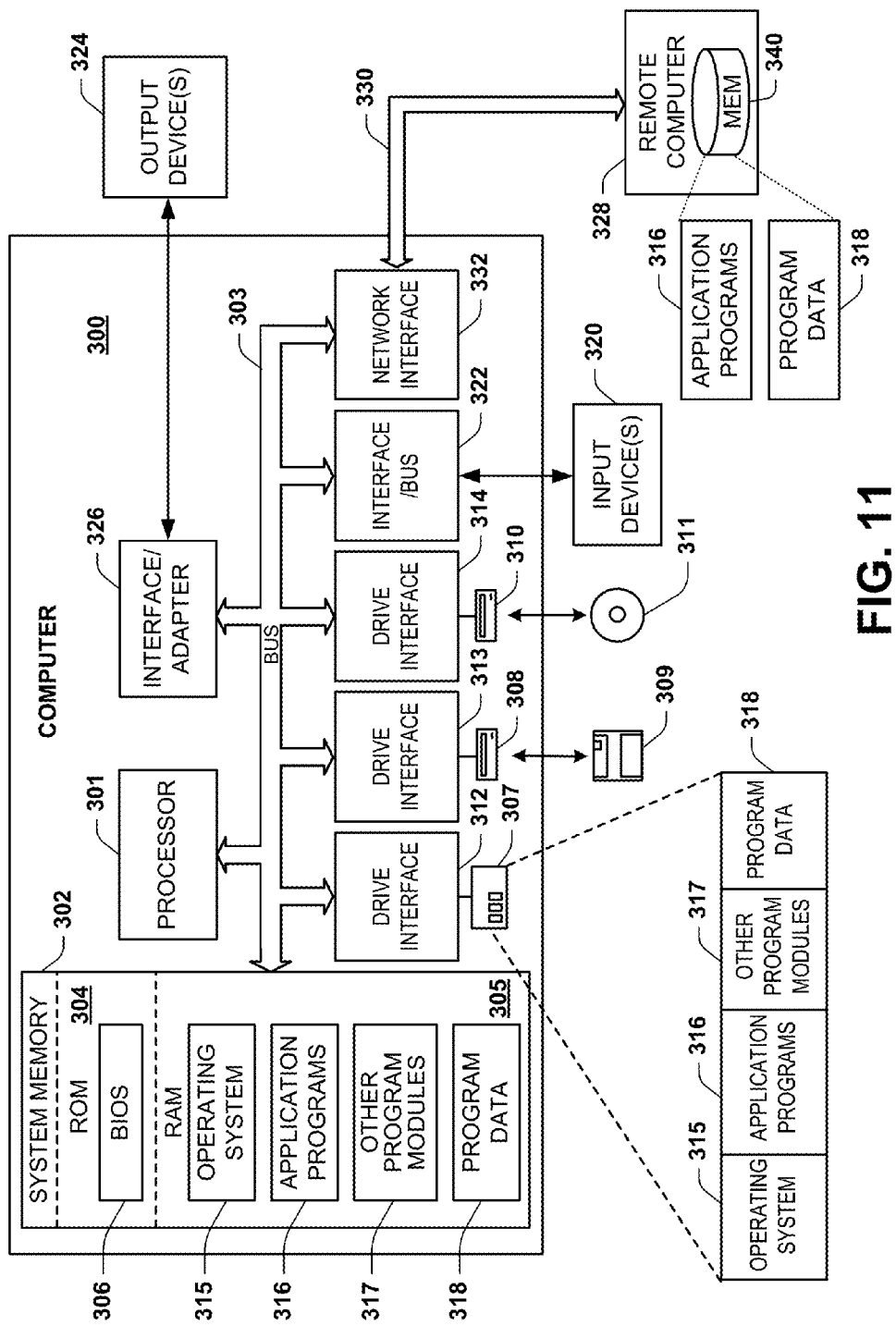

EXPERT SYSTEM TO FACILITATE SOURCE LOCALIZATION OF BRAIN ELECTRICAL ACTIVITY

CROSS-REFERENCE TO RELATED APPLICATION

This application claims the benefit of U.S. Provisional Patent Application Ser. No. 61/553,688, filed Oct. 31, 2011, and entitled SOURCE LOCALIZATION OF BRAIN ELECTRICITY ACTIVITY, the contents of which is incorporated herein by reference in its entirety.

TECHNICAL FIELD

This disclosure relates to source localization of brain electrical activity.

BACKGROUND

Electroencephalography (EEG) is the recording of electrical activity along the scalp. EEG measures voltage fluctuations resulting from ionic current flows within the neurons of the brain. It is desirable to determine the source of certain electrical activity that is discernable from the EEG. For example, EEGs are utilized as part of diagnosis and surgical treatment planning for patients that may suffer from focal epilepsy. The process of finding the location and distribution of the sources that create these activities is called electrical source imaging (ESI) or source localization. However, existing source localization methods using EEG tend to be overly complicated for the user when accurate estimates are required.

Magnetoencephalography (MEG) is a technique for mapping brain activity by recording magnetic fields produced by electrical currents occurring naturally in the brain. MEG can be used for source localization, such by calculating a set of equivalent current dipoles. While MEG may often provide increased accuracy relative EEG, the underlying technology is much more expensive and not as readily available.

SUMMARY

This disclosure relates to source localization of electrical activity.

As one example, a computer-implemented system can localize a source of electrical activity in a patient's body. The system can include a preprocessing component programmed to preprocess electrical data corresponding to electrical signals acquired from a patient. An inverse model (e.g., stored in memory) can represent the source of electrical activity. A forward model (e.g., also stored in memory) can represent geometry and electrical characteristics of a spatial region of interest for the patient's body based on the inverse model. A source localization function can be programmed to compute a location for the source of electrical activity within the spatial region of interest based on the preprocessed electrical data, the inverse model and the forward model. An expert system can evaluate an acceptability of the computed location for the source of electrical activity and to selectively adjust of at least one of the preprocessing, the inverse model and the forward model based on the evaluation of the acceptability. The expert system can also be adapted to cause the source localization function to re-compute the location for the source of electrical activity based on the selective adjustment.

As another example, a non-transitory computer-readable medium having instructions which, when executed, can cause a processor to prepare brain electrical data acquired from a patient and geometry data. Source localization can be performed based on the prepared brain electrical data and geometry data to determine a location of a source of electrical activity. An expert system can be implemented to evaluate an acceptability of the source localization and to adjust at least one of the preparation of the brain electrical data and the geometry data if the acceptability of the source localization is not within a predetermined acceptability level. Output data, corresponding to the location of the source of electrical activity, can be stored if the acceptability of the source localization is within the predetermined acceptability level.

BRIEF DESCRIPTION OF THE DRAWINGS

FIG. 4 depicts an example of wavelet transformation being used to facilitate artifact detection.

FIG. 11 depicts an example computing environment.

DETAILED DESCRIPTION

This disclosure provides systems and methods that can be used to facilitate source localization of electrical activity for the brain. The source localization can be reconstructed and represented in a graphical form, such as superimposed in a brain image (e.g., an MRI). In one example, an expert system can be utilized to evaluate the source localization results and, based on the acceptability of the results, provide automatic adjustments during a data preparation phase to achieve acceptable source localization results. This approach can be implemented with an acceptable accuracy and in the absence of more complex and expensive methods, such as magnetoencephalography (MEG). Additionally, the expert system affords a reduced learning curve and sophistication to operate the system effectively while achieving satisfactory results.

Figure 1:
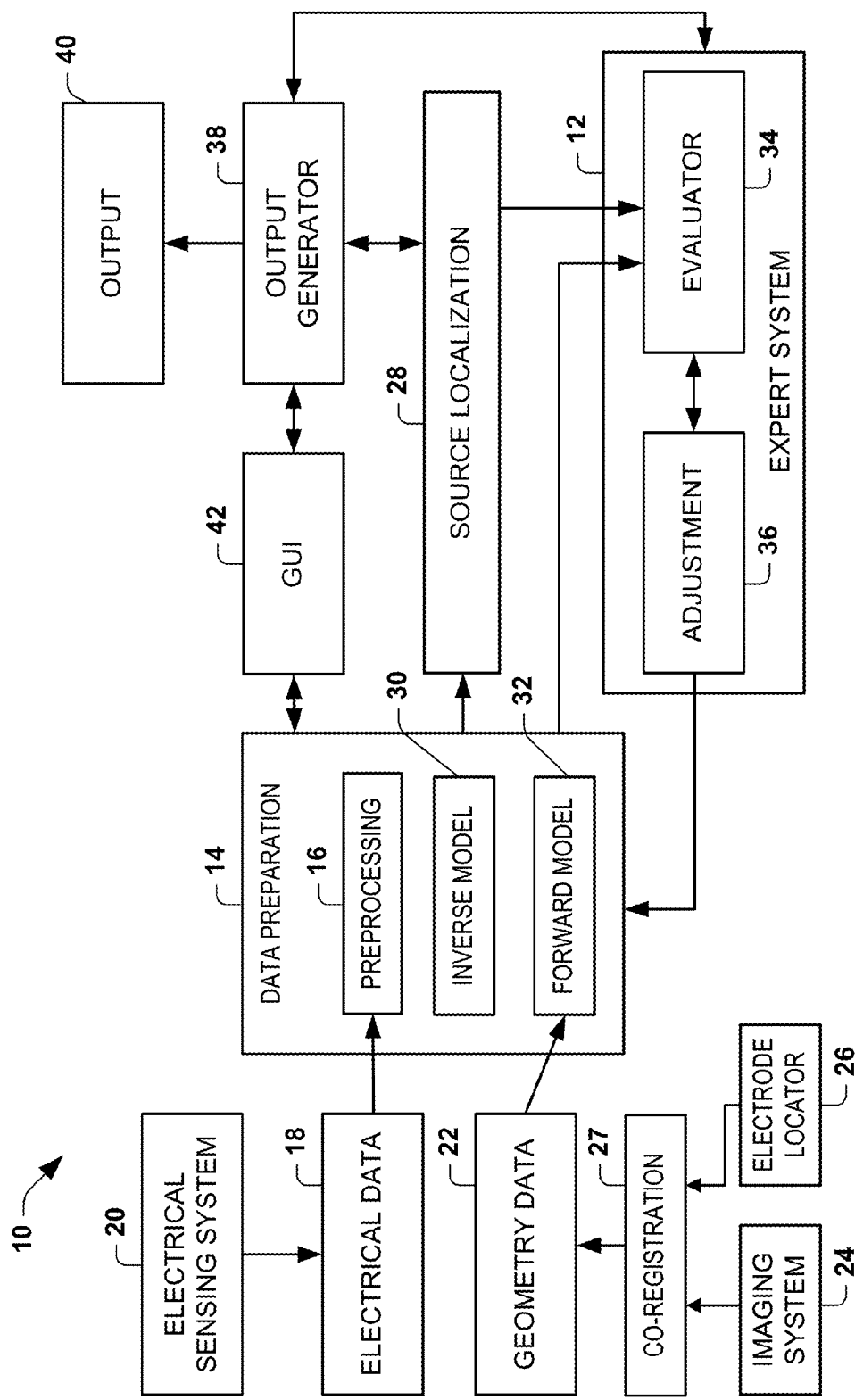
FIG. 1 depicts an example of a system to facilitate localizing brain electrical activity.

FIG. 1 depicts an example of a system 10 that can be utilized to facilitate localizing electrical activity, such as brain electrical activity. As mentioned above, the system 10 employs an expert system 12 to make adjustments to the data preparation phase 14 if it is determined that the source localization results are not acceptable. As used herein, the expert system can be implemented as machine-readable instructions, executable by a processor, to emulate decision-making process of a human expert in the field of source localization. The instructions can be stored in a non-transitory computer-readable medium (e.g., volatile or nonvolatile memory), which can be accessed by a processor to perform the functions disclosed herein. Examples of some types of expert systems that might be used in the system 10 include any artificial intelligence, such as rule-based methods, an inference engine (e.g., fuzzy logic, propositional logic, modal logic or the like), algorithmic methods and the like.

The data preparation phase 14 can include preprocessing 16 of electrical data 18. For example, the electrical data can include data representing EEG signals that can be acquired by an electrical sensing system 20. The electrical sensing system 20 thus can include an arrangement of electrodes that are distributed non-invasively on a patient's head surface to measure brain electrical activity. The patient can include any living being, human or otherwise. The position and number of EEG electrodes can vary. Each EEG electrode in the sensing system 20 corresponds to a sensing channel that provides a signal representing sensed brain electrical activity. As described herein, the preprocessing can include filtering (e.g., high-pass and/or low-pass filters), averaging, principal component analysis, independent component analysis, and other noise and artifact reduction techniques. An initial simplified configuration can be implemented as a default for the preprocessing (e.g., some nominal high-pass filtering).

In order to perform, source localization for measured brain electrical activity, the data preparation 14 can also employ geometry data 22. The geometry data 22 can characterize geometry of relevant anatomy. The geometry data can include actual patient geometry, such as acquired by an imaging system 24. The imaging system 24 can be implemented as any imaging modality (e.g., computed tomography (CT), magnetic resonance imaging (MRI), Positron emission tomography (PET), or the like). For purposes of simplification and consistency, the following discussion will often discuss the system in the context of MRI imaging. As an alternative to using an MRI for a given patient, the imaging system 24 can correspond to a generic or standard MRI that provide generally applicable anatomic information. Thus, the patient specific MRI can provide a more realistic and individualized head model, whereas the generic MRI can produce a general model that is used for all patients and tends to result in less accurate localization.

The geometry data 22 can also include data representing the position of electrodes in the electrical sensing system 20. An electrode locator 26 can be configured to determine coordinates of the electrodes on the patient's head. As one example, the electrode locator 26 can employ an electromagnetic digitizer, such as the Fastrack system available from Polhemus, Inc. of Colchester, Vt. This and other approaches (e.g., image techniques) to localize the electrodes can be employed to provide a relative location of electrodes in a respective coordinate system.

A co-registration function 27 can be programmed to co-register the coordinates, corresponding to electrode locations determined by the electrode locator 26, with the image data from the imaging system 24 into a common spatial coordinate system for the head geometry (e.g., patient-specific or standard geometry). The co-registration function 27 can be implemented as a fully automated, semi-automated or a manual method to align the coordinates of the electrode locations with respect to the image. Such co-registration 27 performed on the electrode coordinates enables the localized source to be visualized in a two-dimensional or three-dimensional image. The image can be a specific patient image or it may be a generic image of anatomy, such as an anatomical atlas (e.g., an atlas brain).

The data preparation 14 also includes other components to enable a source localization method 28 to determine a location of an identified potential. The other components can include an inverse model 30 and a forward model 32. The inverse model and the forward model are used to solve the inverse problem associated with locating a source of a known potential. The inverse problem, however, is ill posed and does not have a unique solution. Accordingly, the system 10 solves the "forward problem" by computing the potential distribution due to a known source inside the brain and then tries to find the best location, orientation, and strength for the source that produces the closest potential distribution to the actual measured data. This means that one has to make some assumptions about the distribution of source (or sources) that produce the EEG signals. These assumptions that constrain the underlying solution correspond to the inverse model 30.

As one example, the inverse model 30 can represent a single dipole as the source of the activity of interest. As another example, the inverse model 30 can be implemented as including more than one dipole (multiple-dipole model) or thousands of dipoles (distributed models) for performing source localization. In addition to the structure of the source, the inverse model can also characterize temporal motion of the source. Thus, the inverse model 30 can represent assumptions about time evolution of the one or more dipoles. The inverse model 30 can also correspond to a moving dipole that allows both the orientation and location of the dipoles to change with time. In a "rotating dipole" approach, the locations of the dipoles are fixed, but their orientations are time-dependent. A "fixed dipole" approach assumes that both orientations and locations of the dipoles are fixed over time. There are also several different distributed models that can be utilized for the inverse model. As disclosed herein, the expert system 12 can selectively employ one of a plurality of such inverse models 30 for use in performing the source localization 28. A single-dipole model can be a default model used for many clinical purposes (e.g., in epilepsy), but other inverse models can be used depending on the purpose of source localization and also depending on the complexity of the EEG signal.

The data preparation 14 also employs the forward model 32 for source localization to represent assumptions related to geometry and electrical properties (e.g., conductivities) for different regions of the head. The system 10 can select one of a plurality of different forward models for use by the source localization 28. As one example, the forward model can model the head as a single sphere or as a sphere having two or more shells. For instance, a spherical model can include three spheres, such as representing the head as consisting of three concentric spheres (skin, skull, and brain) with different conductivities. A four-shell spherical method adds another layer to the previous model (e.g., cerebrospinal fluid).

By way of further example, the forward model can be implemented as a realistic head model. Two examples of realistic models include the boundary element method (BEM) and finite element method (FEM). In each of BEM and FEM, the surfaces of different regions of the head can be reconstructed using the patient's actual MRI or using a standard MRI. In BEM, after reconstructing the boundaries between different head regions, the surfaces can be triangulated; i.e. they are partitioned to small triangles. In FEM, each region is tessellated to small tetrahedral elements. The triangulation/tessellation step is necessary for performing the calculations needed for the forward solution. The FEM method can be considered more accurate than BEM because it allows more accurate reconstruction of geometry, and also because conductivity anisotropy of skull and white matter can be taken into account in this method. A given forward model can be utilized by the source localization 28, which can be a default forward model or another one of a plurality of available models. For example, during operation, the expert system 12 can select a given forward model from an available set of different forward models. The different forward models further can include a plurality of different implementations of BEM forward models and/or a plurality of different implementations of FEM forward models.

As a further example, the forward solution (calculating the potential due to a known source) can be performed in multiple steps. For instance, a transfer matrix can be calculated, as part of the data preparation 14, based on the geometry of different head regions and their conductivities which can be utilized to provide part of the forward model 32. Since the transfer matrix is not dependent on the electrical (e.g. EEG) signal (and only depends on the head parameters), it can be calculated only once for each patient for a given set of electrical measurements. This is important because this calculation may take a while, especially if FEM is chosen as the forward model, due to the complexity of the computations. The calculated transfer matrix can then be utilized by the source localization 28 to calculate the potential fitted to the recorded electrical data 18. The potential can be either be pre-computed at this stage and implemented as part of the forward model, such as for a pre-determined mesh of dipoles. Alternatively, the potential can be computed and evaluated by the source localization 28 at the time of fitting. If the pre-computation approach is utilized, the results can be stored in memory and later compared to the actual data to ascertain the localization results.

The source localization 28 is programmed to localize one or more sources of electrical potential, such as a selected spike. There are different approaches that can be utilized for source localization, which can vary based on the inverse model 30 and the forward model 32 that are utilized. The source localization 28 can compute the location of the source (s) based on the preprocessed electrical data (e.g., provided by the processing component 16), the inverse model 30, and the forward model 32.

The source localization 28 can determine specifications of the source that produces the closest electrical potential to the actual recorded potential. The specifications can include a position (e.g., coordinates) of the localized source in three-dimensional space. The localized position can be identified as one or more points, an area (e.g., a surface area that may be flat or curved) or a volume (e.g., a three-dimensional region). The corresponding type of localized position may vary based on the inverse model that is utilized. As one example, the source localization 28 can be programmed to fit pre-computed (and saved in memory) potentials produced by a grid of dipoles by comparing the pre-computed potentials to the actual electrical data 18 to find a best solution. If the pre-computation method is utilized no fitting is done and this step can be performed very fast, although the pre-computation part may take longer. As another example, the source localization can be programmed to fit the forward solution to the recorded data by minimizing the difference (e.g., via a least squares method). The latter approach tends to be slower than pre-computing potentials, but would decrease the amount of time spent on pre-computation. The approach utilized can be selected by the user, or be determined by the expert system.

The expert system 12 can include an evaluator 34 programmed to evaluate the acceptability of the results provided by the source localization 28. The evaluator 34 can ascertain the acceptability of the localization results by employing one or more evaluation criteria. If the results of the source are not acceptable, an adjustment function can used to modify the data preparation process 14 and the source localization can re-compute the solution according to the adjustments.

As one example, the evaluator 34 can be programmed to compute a goodness of fit (GOF) that provides a measure of how well the electrical potential of the calculated source(s) matches the actual potential. For instance, the GOF can be computed as a number between 0 and 1, such that a GOF of 1 means a perfect fit. However, since the data always includes noise even a perfect fit may not guarantee that the true geometric location of the source has been found. A threshold can be set so that a GOF above the threshold indicates that the localized source is acceptable and below such threshold is unacceptable.

Additionally or alternatively, the evaluator 34 can be programmed to compute a confidence region. The confidence region, in contrast to the GOF, depends on the noise level and is defined as the region that, with a certain probability, contains the source. The evaluator 34 can compute a volume of the confidence region as a good indicator of the EEG noise level, in which a higher noise means larger confidence region. A threshold can be set for a volume confidence region such that a volume computed for a confidence region that exceeds the confidence threshold indicates that the solution is rejected as unacceptable. If the evaluator 34 determines that the volume computed for a confidence region is less than the threshold volume, the localized source is acceptable.

The evaluator 34 can employ one or more of the GOF, the confidence regions as well as other methods to ascertain the acceptability of each solution determined by the source localization 28. As one example, the determination can be computed as a weighted sum of both the GOF and computed confidence region. As another example, the criteria can be selected by the user manually, such as via the GUI 42, or automatically, such as by the expert system 12. If the evaluator 34 determines (e.g., based on one or more criteria as disclosed herein) that the solution for the source localization is acceptable, the specification for the source location can be provided to an output generator 38 to provide a corresponding output 40. The output generator 38 can be programmed to generate the output 40 based on the results of the source localization 28.

As one example, a graphical (and/or text-based) representation of the localized source can be superimposed on a graphical representation of the patient's brain, such as provided by the imaging system 24 (e.g., by displaying the location of the source localization superimposed on one or more images from a patient's MRI). For example, the localized source can be spatially represented on the anatomical image at the location determined to be acceptable. Where multiple acceptable localized sources have been computed, each source can be visualized concurrently or separately. For instance, a user can select (e.g., via GUI) a given localized source from a list of computed sources to cause a representation of the given localized source to be rendered graphically in the image. If multiple localized sources are presented concurrently in the same image, color coding or other means of differentiating them can be utilized.

If the evaluator 34 determines (e.g., based on one or more criteria as disclosed herein) that the solution for the source localization 28 is not acceptable, the expert system 12 can employ one or more adjustment functions 36 to modify one or more aspects of the data preparation to repeat some or all of the calculations. The adjustment function 36 can adjust one or more of the preprocessing 16 on the electrical data 18, change the inverse model 30 and/or change the forward model 32. The source localization 28 thus can be recomputed for the adjusted data preparation 14, and the adjustments and computations can be repeated until at least one acceptable source localization is computed for a given instance of the data preparation stage.

In other examples, the source localization 28 can be programmed (e.g., in response to a user input) to ascertain multiple acceptable source localizations. For instance, the expert system 12 can adjust the data preparation phase 14, such as disclosed above, and the source localization and compute a corresponding source localization that is acceptable, which results can be stored in memory. The expert system can further adjust the data preparation phase 14 and another source localization can be computed. This can be repeated any number of two or more times to provide a results set of location coordinates for each acceptable source localization result. These results can be provided to the output generator for visualization on an anatomical image. As an example, since each acceptable source location is computed for the same selected signal, the different acceptable source localizations can be aggregated statistically (e.g., a median location) to provide a resulting source localization that can be provided in the output 40 for the user. As another example, a user can compare the acceptable results for each of a plurality of different data preparation parameter sets.

Figure 2:
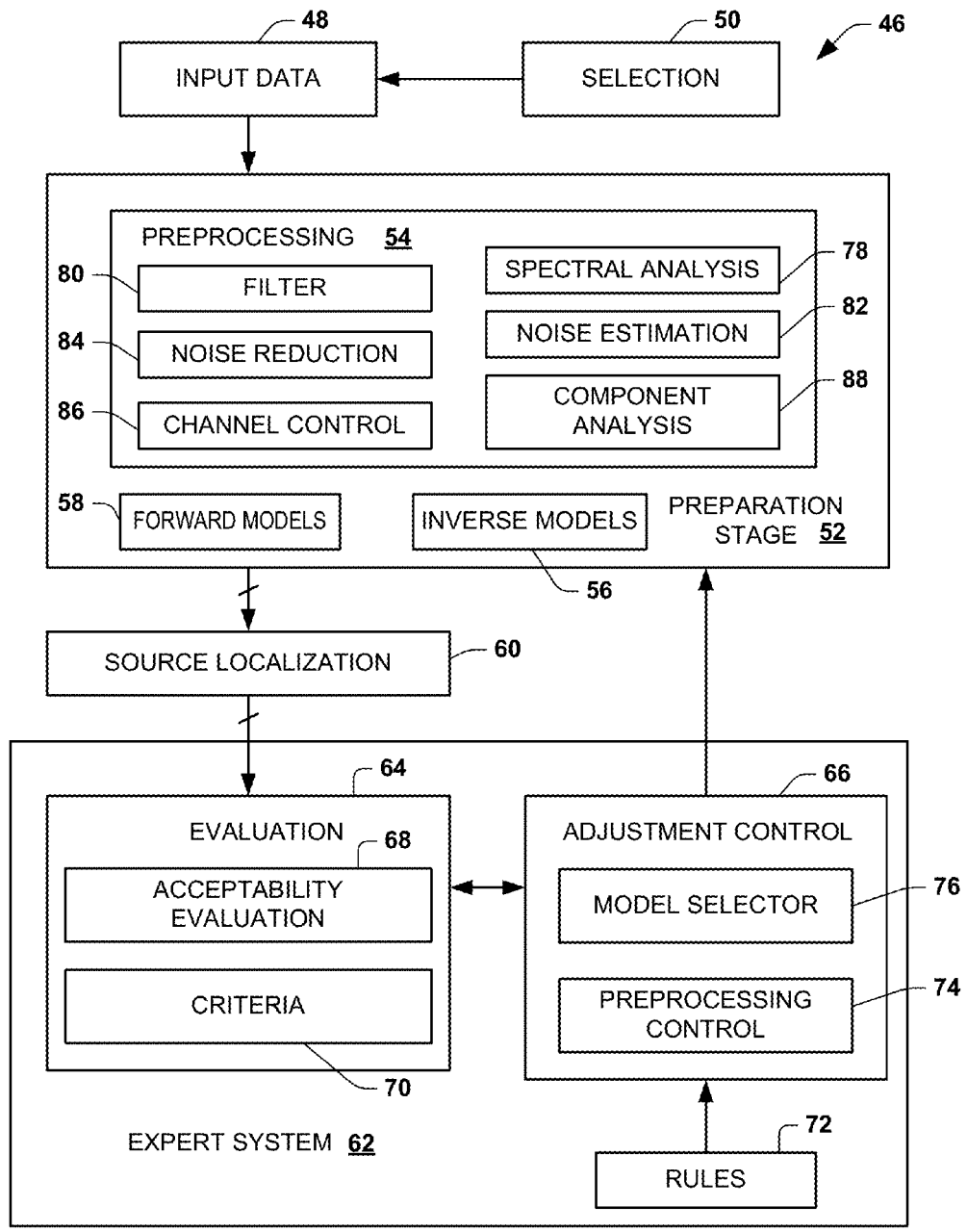
FIG. 2 depicts another example of a system for source localization.

FIG. 2 demonstrates another example of a system 46 to facilitate computing an acceptable solution for source localization of a voltage potential. The system can operate on input data 48, such as can corresponding to the electrical data 18 and geometry data 22 of FIG. 1. The system 46 can include a selection component 50 programmed to select which of the input data 48 is to be utilized for source localization. The selection 50 can be automated, semi-automated, or be manual in response to a user input (e.g., selecting one or more signal interval for which source localization is to be performed).

The system 46 includes a preparation stage 52, which includes preprocessing 54, an inverse model 56 and a forward model 58. A source localization method 60 is programmed to compute a location for a source of a selected electrical signal (e.g., voltage potential) based on the preprocessed electrical data, inverse model 56 and forward model 58. For instance, the preprocessing 54, inverse model 56 and forward model 58 can be instantiated to defaults for use by the source localization 60 to compute a solution.

Figure 8A:
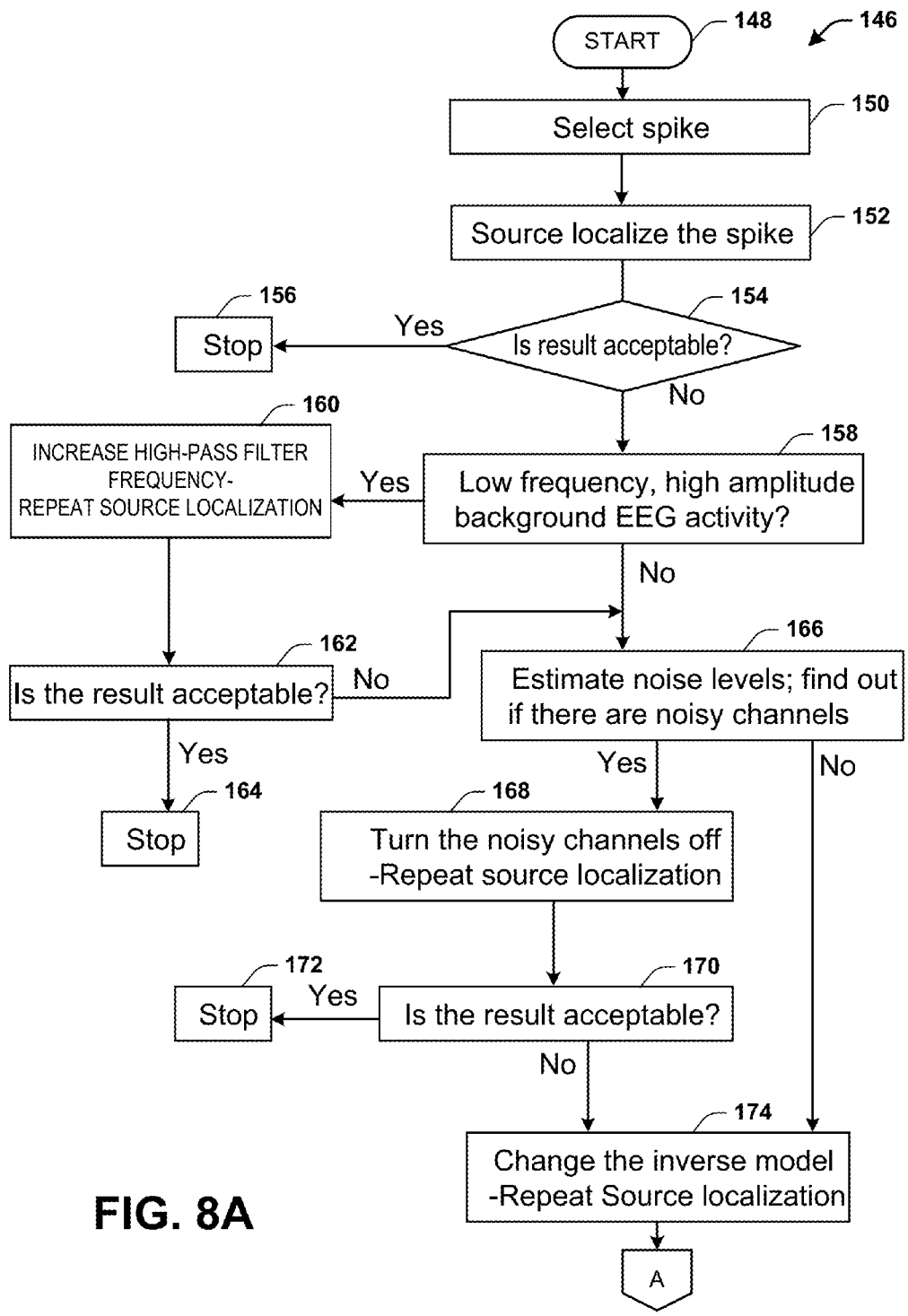
FIGS. 8A and 8B collectively depict a flow diagram demonstrating an example of a method that can be implemented to facilitate source localization.
Figure 8B:
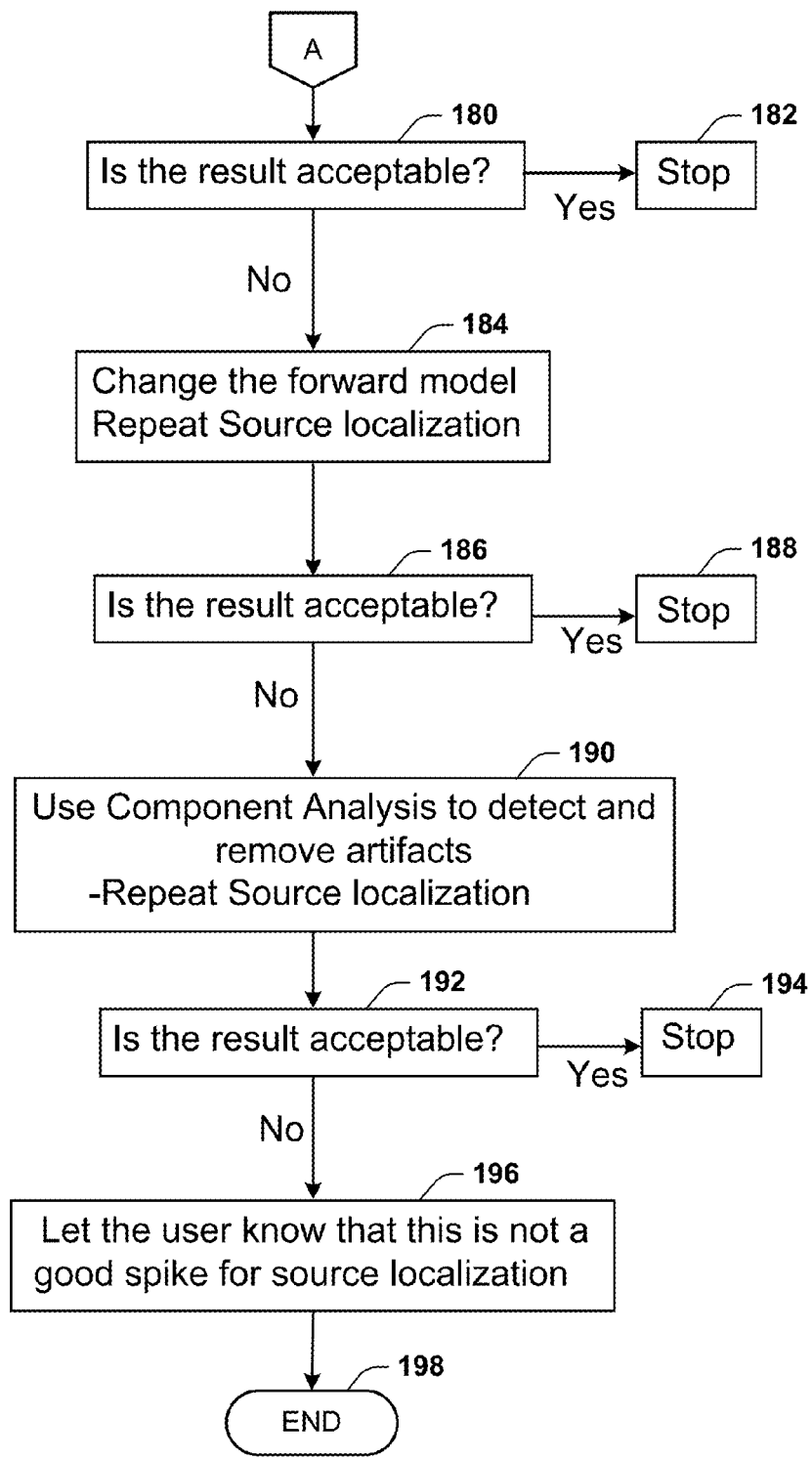

An expert system 62 is configured to control the preparation stage 52 for source localization 60 to facilitate computing an acceptable solution, such as disclosed herein. One or more of the preprocessing 54, inverse model 56 and forward model 58 can be programmable by the expert system 62. The expert system 62 includes an evaluation function 64 and adjustment control 66 programmed to adjust the preparation stage 52 if the solution computed by the source localization method 60 is unacceptable. An example algorithm that can be implemented by the expert system 62 for evaluating and adjusting the data preparation for performing source localization is shown in FIGS. 8A and 8B. Other methods and artificial intelligence can be utilized adjust selected parameters of the preprocessing, forward model and inverse model.

In the example of FIG. 2, the evaluation function 64 can include an acceptability evaluation 68 programmed to ascertain the acceptability of the solution computed by the source localization 60. The evaluation function 64 can also include evaluation criteria 70 that define what constitutes an acceptable or unacceptable solution. The criteria 70 can vary based on the technique or combination of techniques utilized for ascertaining acceptability. As an example, the acceptability evaluation 68 can calculate a GOF, a confidence region or a combination thereof for the calculated source localization. The acceptability evaluation 68 thus can compute a metric or a combination of acceptability metrics with the criteria 70 setting corresponding thresholds for acceptability. The thresholds for acceptability can be user programmable or predetermined default thresholds can be used.

As disclosed herein, the adjustment control 66 can adjust one or more portions of the preparation stage 52 if the evaluation function determines that the source localization solution is not acceptable. The adjustment control 66 can employ rules 72 programmed to specify what one or more portions of the preparation stage 52 should be adjusted. The amount and type of adjustment can be determined by the adjustment control 66, by analysis methods in the preparation stage 52 or such determinations can be distributed between the adjustment control and the preparation stage. For example, the rules 72 can be programmed to specify a type of adjustment and the preparation stage 52 can determine the amount of adjustment that is to be implemented.

In the example of FIG. 2, the adjustment control 66 includes a preprocessing control 74 and a model selector 76. The adjustment control 66 can employ the preprocessing control 74 to adjust one or more preprocessing parameter of the preprocessing 54 based on the rules 72. The adjustment control can also specify the amount of adjustment or the amount can be a predetermined incremental amount, for example. The model selector 76 can select a given forward model from a plurality of available models (e.g., stored as a library of forward models) 58 and a particular implementation thereof based on the rules 72. The model selector 76 can also select the inverse model from a plurality of available inverse models (e.g., stored as a library of inverse models) 56 and a particular implementation thereof based on the rules 72.

By way of further example, if the default settings for the preparation stage do not provide an acceptable solution for the source localization function 60, the preprocessing control 74 can instruct the preprocessing 54 to adjust one or more parameters of a filter 80 programmed to filter the sensed electrical signals. The filter 80, for example, can include a low-pass filter, a high-pass filter, a notch filter or a complex filter having an arrangement of poles and zeros. The same filter can be applied as a common filter to each of the input channels or different filter characteristics can be applied selectively to each channel. The preprocessing 54 can include a spectral analysis function 78 programmed to determine frequency characteristics of the sensed signals, including the particular signal segment that was selected for source localization, and adjust the filter 80 based on the frequency characteristics. For example, the filter 80 can be adjusted to remove unwanted signals from the activity of interest to improve the signal to noise ratio. The source localization function 60 can re-compute the solution with the modified instance of the filter 80.

If the evaluation function 64 determines that the solution is still unacceptable, the preprocessing control 74 can instruct a noise estimation function 82 of the preprocessing 54 to estimate the noise for each of the input channels. If such calculation demonstrates that the noise for one or more channels exceeds the noise for other channels by a predetermined amount (e.g., relative noise per channel), channel control 86 can remove such noisy channels and the source localization 60 can be repeated without such noisy channels. Additionally, or alternatively, if the noise estimation function 82 determines that the noise for one or more channels exceeds a noise level, but not a relative noise threshold, the preprocessing 54 can employ other noise reduction techniques 84 based on the characteristics of the noise that is detected.

As a further example, the preprocessing control 74 can determine that different (e.g., more sophisticated) types of noise reduction may be required based on application of the rules 72. For example, the preprocessing 54 can also apply principal or independent component analysis (PCA or ICA) 88 to detect and remove artifacts that can occur during signal acquisition. The component analysis 88 can include PCA and/or ICA methods. For example, artifacts can occur in electrical (e.g., EEG) signals due to environmental stimulations, such as audible noise and visual stimulation as well as patient actions, such as movement (blinking, scratching or the like).

By way of example, component analysis, such as ICA, can be employed to separate these artifacts from the cerebral activity. The artifacts can then automatically detected using time-frequency analysis (e.g., continuous or discrete wavelet transformation) and/or by determining the distribution of electrical potential due to that component on the surface of the head. For instance, some artifacts, such as eye blinks and heart electrical activity (e.g., EKG), are known to have a specific distribution on the scalp. Any component that is determined shows a strong correlation with such known distribution can be tagged as a possible artifact.

Figure 3A:
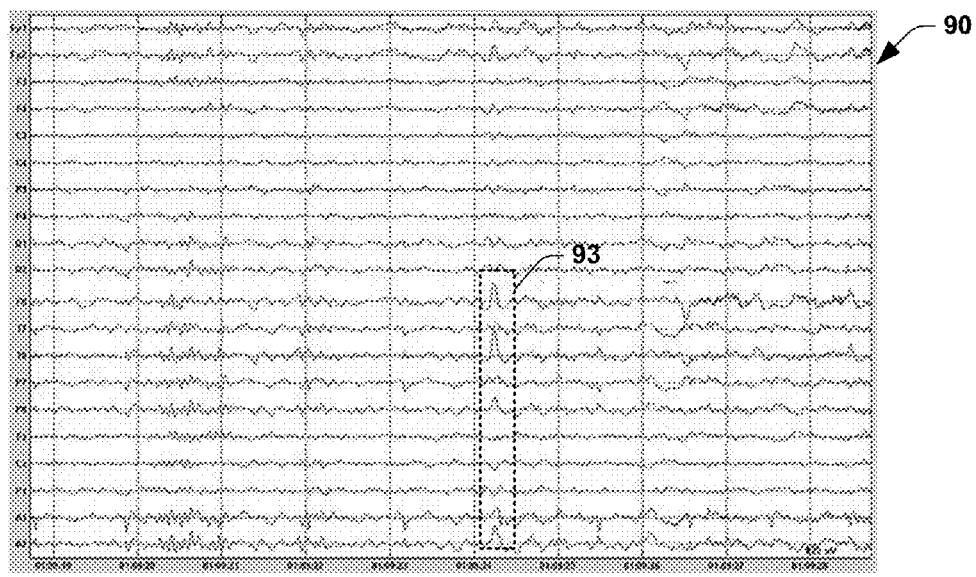
FIG. 3A depicts an example of artifact contaminated signals.
Figure 3B:
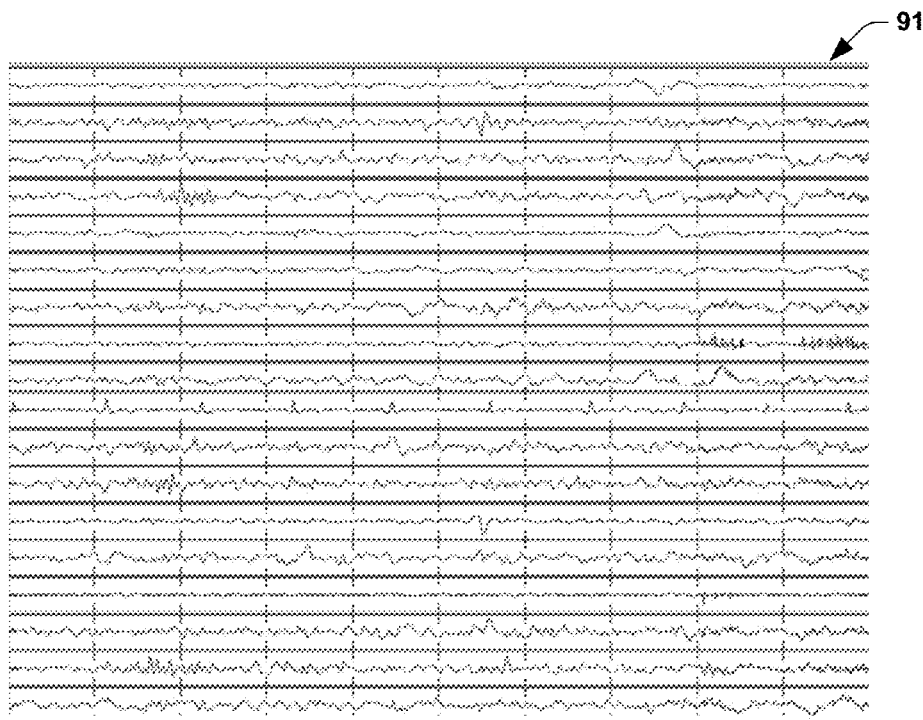
FIG. 3B depicts an example of artifacts extracted from the signals of FIG. 3A.

FIGS. 3A and 3B depict examples of EEG signals 90 and 91 to help demonstrate some effects of artifacts and how by separating such artifacts, they can be removed from the acquired EEG signal. Many artifacts, including eye blinks and EKG, also have a specific morphology. EKG artifacts, for example, are spiky and periodic, such as shown in the EEG signals contaminated with EKG artifact in the example of FIG. 3A. Applying a wavelet transformation to such signal component can produce a signal with much higher peaks to facilitate detection and removal of the peaks corresponding to such artifacts. In the example of FIG. 3A, an EKG-induced peak, demonstrated at 93, occurs nearly concurrently as an epileptic spike that needs to be source localized. If not removed, the artifact could alter the source localization result. As demonstrated in the example of FIG. 3B, ICA can be used to separate different components of the signal. The signals 91 in FIG. 3B thus correspond to independent components computed using ICA on the signals 90 from FIG. 3A.

A continuous wavelet transformation (e.g., using Coiflet-type wavelets) can be applied to all separated components using ICA. This transformation thus can enhance the peaks of the EKG-related component, such as to facilitate their detection. As a further example, FIG. 4 demonstrates an example of a wavelet transformation 94 that can be applied to the ICA-separated signals (e.g., the signals 91 of FIG. 3B) to detect corresponding components thereof, demonstrated at 95. The next step is to check that the peaks occur periodically such that the periodically occurring components can be removed by subtracting such frequency domain components from the wavelet transformation of the acquired signals.

Figure 5:
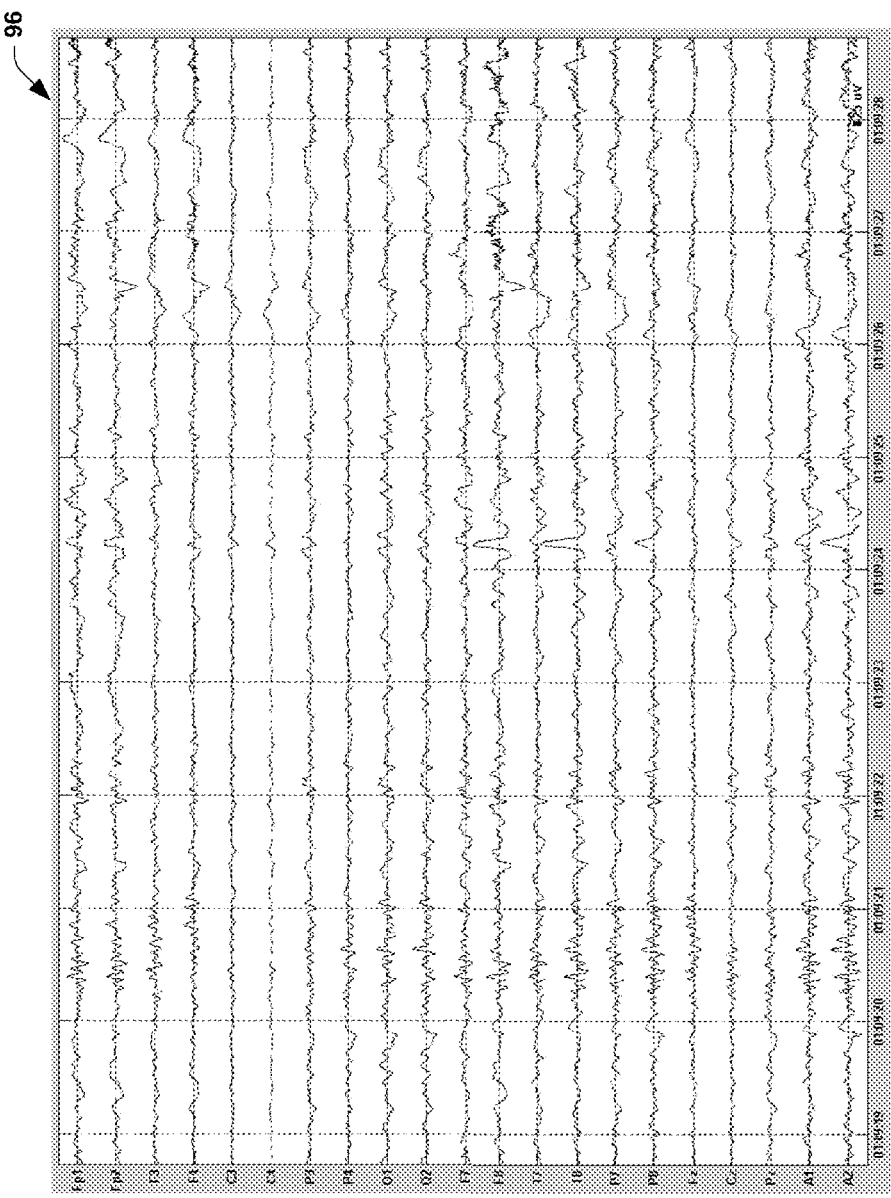
FIG. 5 depicts an example of the signals of FIG. 3a after implementing artifact removal.

Once the artifact is found, as mentioned above, it is rejected (e.g., by subtracting the components from the original signal in the transform domain). The resulting artifact-free signals are reconstructed (e.g., via inverse wavelet transformation). FIG. 5 demonstrates an example of EEG signals 96 that can be generated from acquired signals 90 of FIG. 3A based on preprocessing the signals by performing ICA, wavelet transformation and inverse transformation, as disclosed above. The source localization 60 of FIG. 2 can proceed on the reconstructed artifact-free signals, as disclosed herein. Similar algorithms can be used for detection and removal of other artifacts, such as eye blinks or the like. The artifact detection and removal can be fully automated. For example, the artifact detection and removal can be activated continuously. Alternatively, in other examples, artifact removal can be activated (or deactivated) in response to a user input, such as via activating a GUI element.

As used herein, artifact-free indicates that artifacts have been removed; however, it does not require 100% removal but rather simply improved content. Additionally, the artifact removal further can focus on each signal interval of interest (selected temporally) since artifacts temporally outside of the signal interval being localized have little effect on source localization.

Referring back to FIG. 2, since the expert system 62 determines what preprocessing techniques to utilize and the settings can be automatically determined, expertise of such techniques by users is not required. When the expert system 62 determines to adjust the preprocessing 54, only the fitting for the source localization and preprocessing of the signals need to be repeated for each selected signal activity that is going to be source localized.

The expert system 62 can also be programmed to employ the model selector 76 to selectively change one or both of the inverse model 56 and the forward model 58 if the evaluation function determines that the solution computed by the source localization is unacceptable. When the forward model is changed, the pre-computed potentials and transfer matrix should be re-computed as disclosed herein, unless they are already computed and saved for the new forward model. In other words, these calculations are pre-computed only once for a specific forward model 58. The preprocessing 54 can return to its default settings for performing the source localization. Alternatively, one or more of the filter 80, noise reduction 84 and channel control 86 can remain at previous values for use in preprocessing the electrical input signals for employing the source localization function. When one or both models 56 and 58 are changed, the source localization 60 computes a solution. The evaluation function 64 of the expert system 62 can again determine if the solution is acceptable and, if necessary, automatically adjust the preparation stage 52, as disclosed herein, such that user interaction can be reduced relative to other source localization approaches.

As disclosed herein, the systems and methods can be utilized to source localize any number of one or more spikes from a set of electrical data. Each such spike can be identified by the selector 76. The selector 76, for example, can select the one or more spikes manually in response to a user input or via automated selection methods. Since noise levels vary with time, the preprocessing 54 will be performed for each electrical signal segment that is to be source localized by the source localization method 60.

For example, if one elects to source localize a plurality of epileptic spikes in an EEG recording (e.g., automated or manual spike selection), settings of the filter 80 may have to be adjusted for each spike depending the frequency of the noise determined by the spectral analysis function 78 for each spike. In addition to choosing filter settings, the expert system 62 also can determine when and how to apply component analysis 88 as well as other more sophisticated signal preprocessing (e.g., wavelet analysis) and noise reduction techniques. Such automated aspects via the expert system 62 further facilitate performing accurate source localization 60 for average users and also reduces the time, effort and expertise required to achieve acceptable source localization results.

Figure 6:
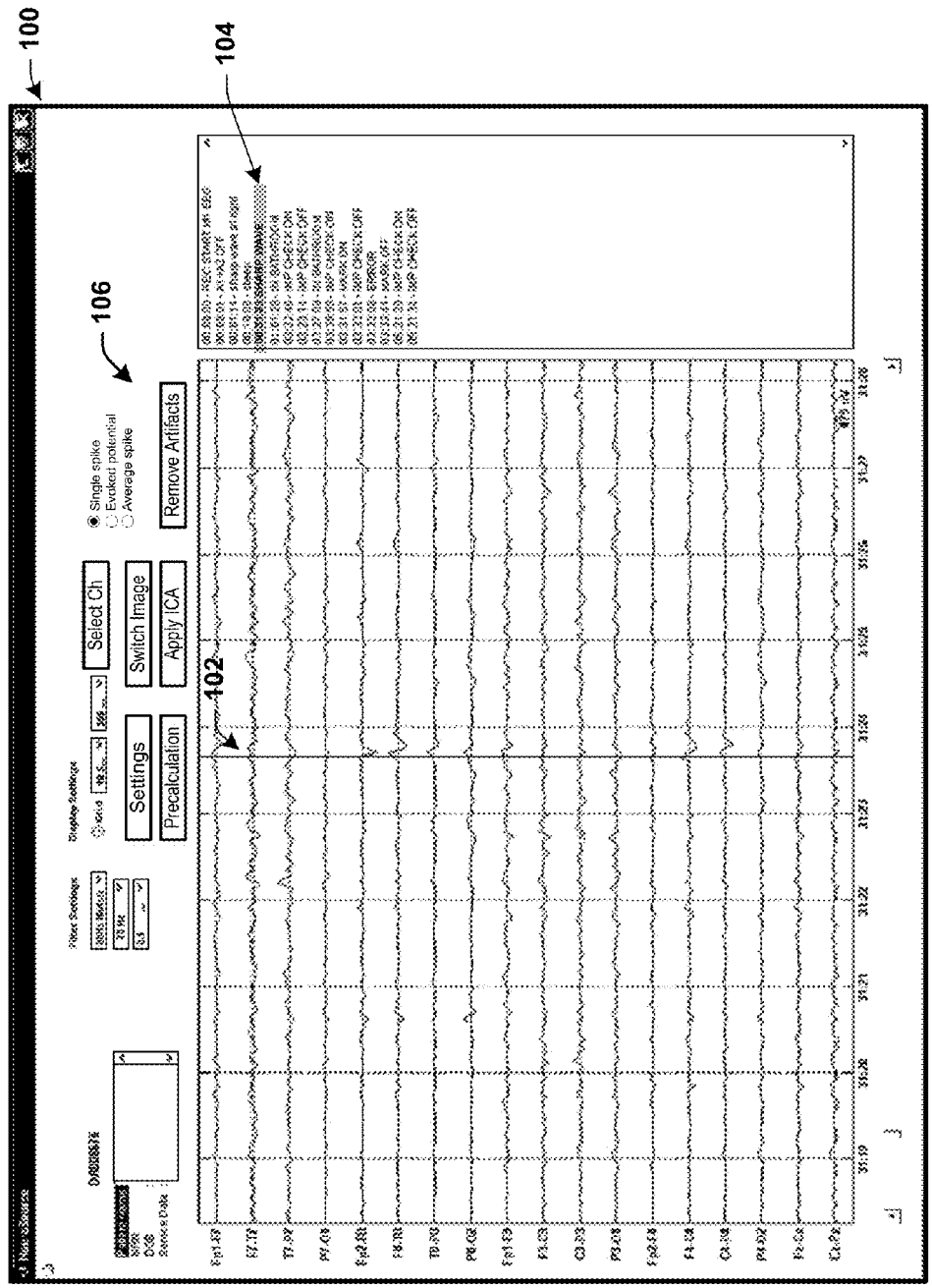
FIG. 6 depicts an example graphical user interface demonstrating EEG signals.

As a further example, FIG. 6 demonstrates an example of a graphical user interface 100 demonstrating part of an EEG recording for a patient. In the example of FIG. 6, a sharp wave, indicated at 102, can be identified by the selector GUI element 104 at about 31:23 for performing source localization. Such selection of the sharp wave 104 can be automated via signal processing or it can be selected via a mouse or other user interface function. For example, a GUI (e.g., corresponding to the selector of FIG. 2) can include different source localization settings, such as to localize a single spike, an evoked potential or an average spike.

The GUI 100 can also include a plurality of GUI elements 106, such as are demonstrated as GUI buttons. In the example of FIG. 6 the GUI elements 106 include a settings button, a precalculation button, a switch image button, an apply CA button and a remove artifacts button. Each of the GUI elements 106 are programmed to activate functions and method disclosed herein in response to a user selecting a respective button. Additional flexibility can be achieved using the GUI 100, such as allowing a user the ability to selectively apply component analysis (e.g., ICA or PCA) to the acquired signals in response to activating the Apply CA button. Additionally or alternatively, a user can selectively enable or disable removal artifacts in response to activating or deactivating, respectively, the remove artifacts button. The type of source or sources being localized (e.g., a single spike, an evoked potential an average spike) can be selected in response to a user input selecting the type. Unlike existing systems, which require complicated manual adjustments to parameters and functions, the approach disclosed herein employs an expert system to select parameters and configure its functions to achieve acceptable source localization results.

Figure 7:
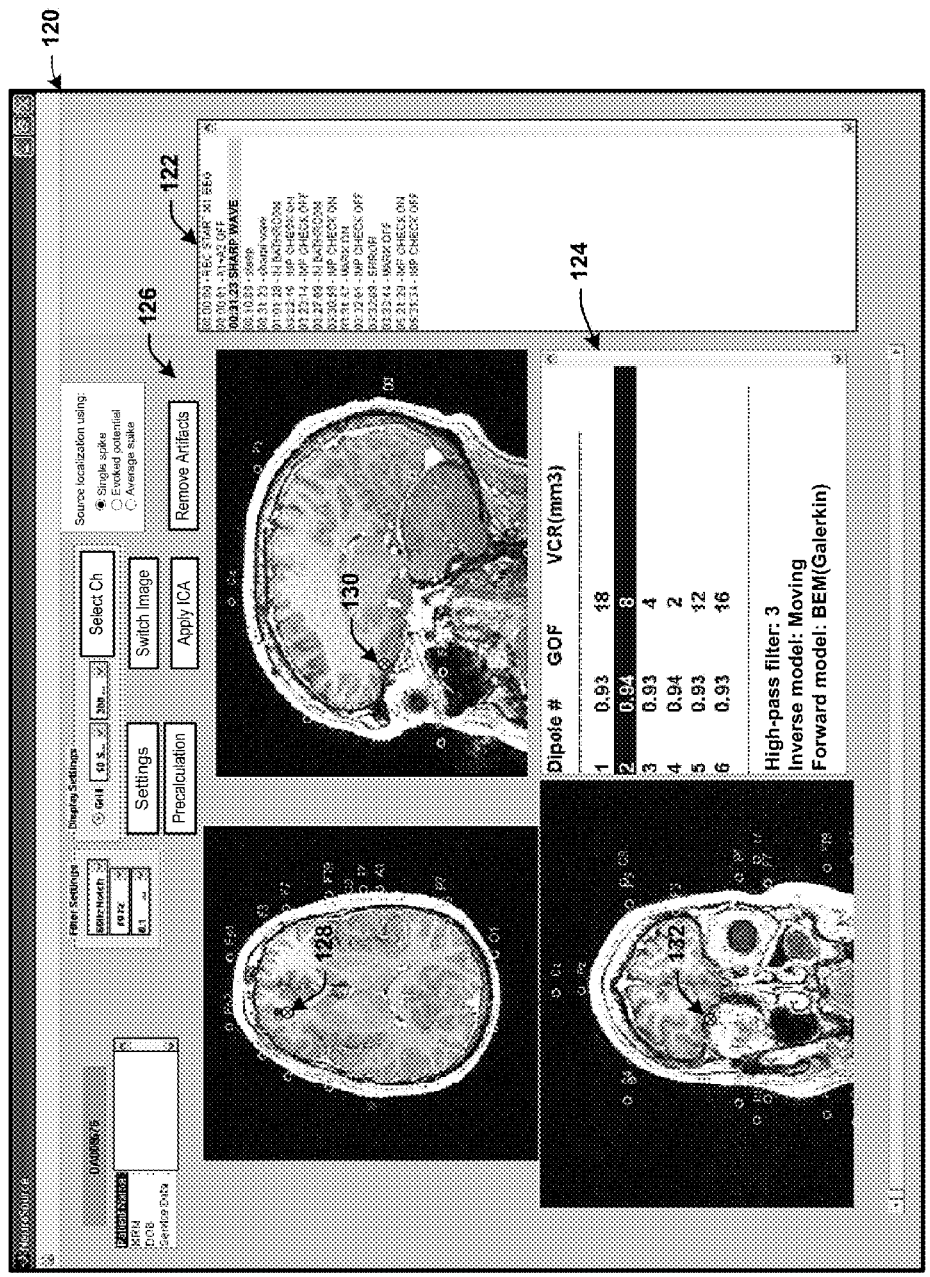
FIG. 7 depicts an example of a graphical user interface demonstrating source localization on an image.

FIG. 7 demonstrates a screen shot of a GUI 120 that can be implemented based on the systems and methods disclosed herein for electrical source imaging. Similar to the example of FIG. 6, the GUI 120 includes a list of waveform intervals that can be selected for source localization. In the example of FIG. 7, a sharp wave at 00:31.23 is shown selected for localization. Also demonstrated is a GUI region (e.g., a window) 124 that provides further information about the source localization process. In the example of FIG. 7, the GUI region 124 includes a list of different dipoles and calculations for two acceptability criteria (e.g., GOF and volume of the confidence region) for computations made for each dipole. Also demonstrated in the GUI region 124 are some details about preprocessing employed by the system for the source localization process, such as including an indication of the high-pass filter, inverse model and forward model. As disclosed in relation to the GUI 100 of FIG. 6, the GUI 120 can also include the same or similar to GUI elements (e.g., buttons) for selectively controlling some high-level pre-processing functionality and selecting the type of source being localized.

The GUI 120 can also display one or more anatomical images that include an indicia (e.g., graphical and/or text) 128, 130 and 132 to identify the localized source for each selected signal interval, such as can be selected at 122. For example, the images can be actual images (e.g., MRI images) of the patient's brain with a graphical representation of one or more source localized spikes superimposed on the brain images, as demonstrated at 128, 130 and 132. In other examples, a generic anatomical image can be used to show the results of the source localization. In either case, the images can be one or more two-dimensional or three-dimensional images.

As mentioned above, FIGS. 8A and 8B demonstrate an example of a workflow method 146 that can be implemented by an expert system (e.g., by the expert system 12 of FIG. 1 or 62 of FIG. 2) in connection with performing source localization. The method 148 begins at 148 such as in connection with initializing variables to starting and/or default values for the source localization process. This can include, for example, employing default predetermined pre-processing parameters, a default inverse model and a default forward model.

At 150, one or more spikes can be selected. As disclosed herein the spike selection can be an automated process or it can be made in response to a user selection. At 152, the source localization can be performed on the selected spike using the default preprocessing, inverse model and forward model settings. At 154, a determination is made whether the results of the calculations at 152 are acceptable. The acceptability determination at 154 (and at other operations in the method 146) can be based on computing and evaluating one or more acceptability criteria, such as GOF, confidence region or a combination thereof. If the results of the determination at 154 are acceptable, the method can proceed to 156 where the method terminates and the localized source for the spike can be stored in memory and used to provide an output, such as disclosed herein (see, e.g., FIG. 7). If the results are not acceptable, the method can proceed to 158.

For example, at 158 the signals can be analyzed to determine if there is any low frequency, high amplitude background electrical activity. If such activity is detected, the method can proceed to 160 in which the high-pass filter parameters can be adjusted to increase the high-pass filter frequency. The source localization at 152 can then be repeated with the adjusted filter parameters. The results of such source localization can be evaluated at 162 to determine if the results are acceptable. If the results are acceptable the method can end at 164. If the results, however, are not acceptable based on the filter adjustments, the method can proceed to 166.

At 166, noise levels can be estimated to determine and identify if there are any noisy channels (e.g., comparing signal-to-noise ratio relative to a noise threshold) that might adversely affect the measurements. If one or more noisy channels are identified at 166, the method proceeds to 168 to turn off the identified noisy channels. The source localization calculation (at 152) can be repeated in the absence of the noisy channels. The results of such source localization can be evaluated at 170 to determine if the results are acceptable. If the results are acceptable the method can end at 172. If the results are not acceptable at 170, the method can proceed to 174. Additionally, if no noisy channels were identified at 166, the method can similarly proceed from 166 to 174.

At 174, the inverse model (e.g., the model 30 of FIG. 1 or model 56 of FIG. 2) can be changed. For example, the expert system method can include a library of inverse models, such as a single dipole model, a multi-dipole model and distributed models, which can be selected for performing source localization. Additionally, for a given single or multi-dipole model, it further can be correspond to a moving dipole, a fixed dipole or a rotating dipole. The selection of the inverse model can be automated or be implemented in response to a user input that identifies which inverse model is to be utilized and then source localization 152 can be repeated for the next inverse model.

After the source localization is repeated the method proceeds (via connector "A") to 180 of FIG. 8B to determination whether the adjusted inverse model from 174 provides acceptable source localization results. This process at 174 can be repeated for any number or one or more different inverse models. If changing the inverse model provides acceptable results, the method can end at 182. If the results are not acceptable at 180, the method can proceed to 184. At 184, the inverse model providing the most acceptable results (e.g., determined from 174 and 180) can be selected for subsequent source localization. In other examples, a default inverse model can be utilized.

At 184, the forward model (e.g., the model 32 of FIG. 1 or model 58 of FIG. 2) can be changed. For example, the expert system method can include a library of forward models, such as can include one or more spherical (e.g., 1-shell, 3-shell or 4-shell) models and/or one or more realistic (e.g., BEM or FEM) models. After the forward model has been changed, the source localization at 152 can be computed for the modified forward model. The process at 184 can be repeated for any number or one or more different forward models or until acceptable results are achieved based on evaluation at 186. If changing the forward model provides acceptable results, the method can end at 188. If the results are not acceptable at 186, the method can proceed to 190. The forward model providing the most acceptable results (e.g., determined from 184 and 186) can be selected for subsequent source localization in the workflow. In other examples, a default forward model can be utilized.

At 190, preprocessing can be implemented to remove artifacts. For example, the artifact removal can employ component analysis, such as ICA or PCA. Wavelet transform can further be used to improve the detection and removal of artifacts, thus increasing the clinical utility. Because EEG noise levels vary with time, the pre-processing has to be re-done for any EEG segment that is to be source localized. By way of example, if one wants to use ESI for 10 epileptic spikes in an EEG recording, the filter settings may have to be changed for each spike depending on the characteristics (e.g. dominant frequency) of the noise. The expert system can automate the removal of artifacts, such as including, for example, what filter settings to use or how and when to apply PCA, ICA or other signal processing techniques. In other examples, the artifact removal at 190 can be implemented to set artifact removal parameters in response to user inputs.

The process at 190 can be repeated for any number or one or more different artifact removal techniques or until acceptable results are achieved based on evaluation at 192. If changing the artifact removal is determined to provide acceptable results at 192, the method can end at 194. If the results are not acceptable at 192, the method can proceed to 196. At 196, the method can inform the user that a given spike or set of spikes for which the method 146 has been implemented are not good candidates for source localization.

From FIGS. 8A and 8B, it will be appreciated that the data preparation (e.g., preprocessing and models) can be adjusted by the expert system in an order of increasing complexity. Thus, by first implementing less complex adjustments to achieve an acceptable solution for source localization, the overall processing time can be decreased. Additionally, since an expert system is employed to decide if the result is acceptable and, if necessary, automatically configures the preprocessing parameters and repeats the relevant computations, user interaction and knowledge of complex signal process and modeling techniques can be significantly reduced while still achieving improved results.

Figure 9:
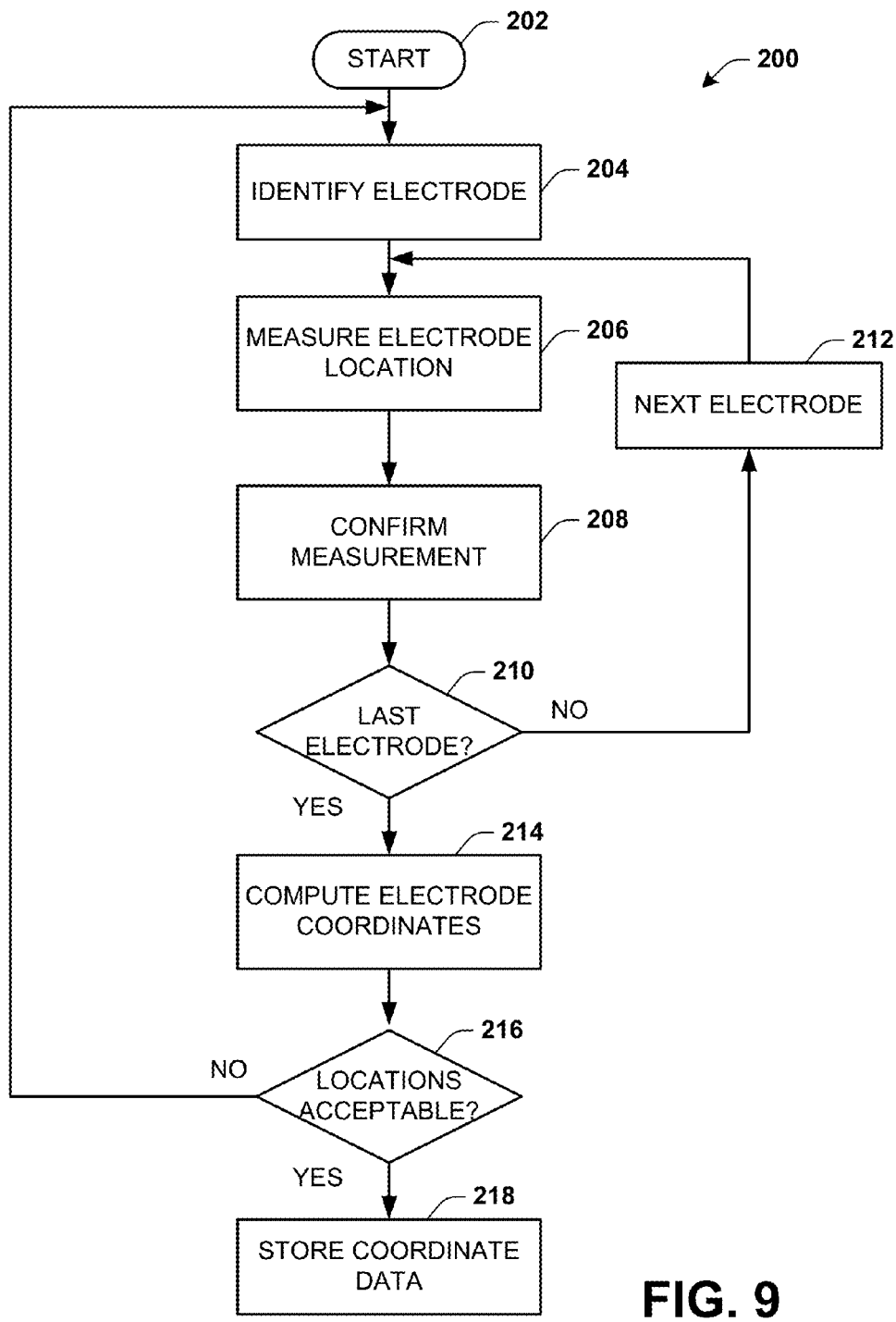
FIG. 9 depicts an example of a method to generate electrode location data.
Figure 10:
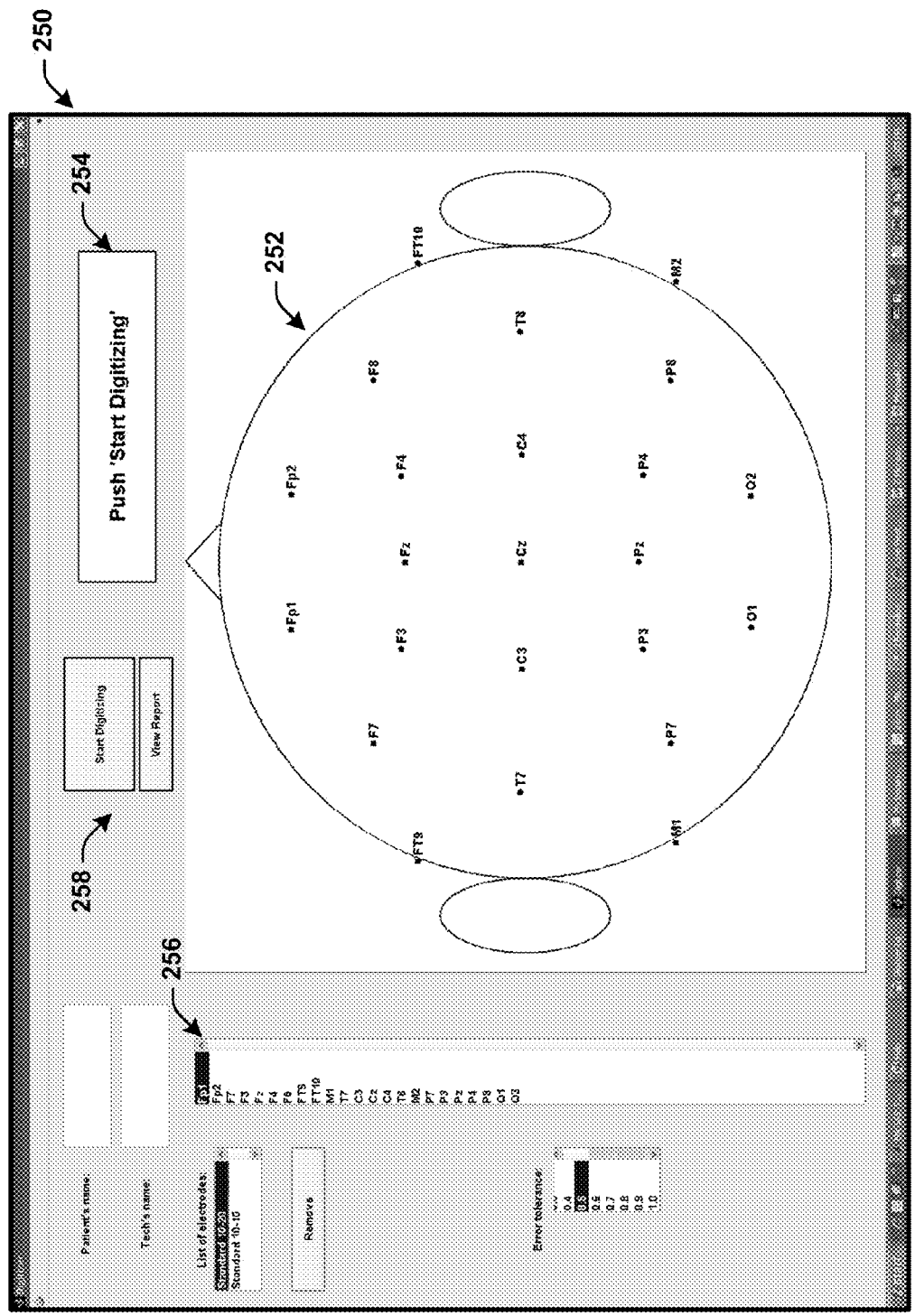
FIG. 10 depicts an example of a graphical user interface to facilitate digitization of electrode locations.

FIG. 9 depicts an example of a method 200 to generate electrode location data (e.g., data from locator 26 of FIG. 1). The acquisition of electrode location data can be facilitated with use of a GUI, such as disclosed in relation to the example GUI 250 of FIG. 10. The example of FIG. 9 relates to determining electrode location data from an electromagnetic digitizer or similar device; however, other techniques can also be utilized to obtain coordinates of the electrodes, such as using an imaging modality (x-ray, CT or the like).

The method begins at 202 after electrodes have been placed on the patient's body at a desired locations. For example, placement of the electrodes can be individually or assisted by using a cap or net that containing the electrodes. At 204, an electrode can be identified and a measurement can be made at 206 for the identified electrode. For the example GUI 250 of FIG. 10, the GUI can include a graphical map 252 of a skull that includes locations of each of a plurality of electrodes for a given configuration (e.g., a standard 10-20 or 10-10 configuration). A display box 254 can also be provided to provide step-by-step instructions to the user, such as including commands to start digitization, when to measure each electrode location and the like. At 208, after a measurement has been made at 206, the method can include a measurement confirmation operation. For example, the GUI can provide instructions to the user to manually confirm that user had actually digitized the correct electrode per the instructions presented in the display box 254. This can be done for each or for a selected portion of the measurements. In other examples, a confirmation response can be requested if it has been determined that an electrode is a greater distance from its expected location.

At 210, a determination is made whether the measurement is for a last electrode. If the additional electrodes require digitization measurements, the method proceeds to 212 to request measurement of the next electrode (e.g., in the display box 254 of FIG. 10). The process at 206-212 can be repeated until it is determined that the last electrode has been digitized. At 214, electrode coordinates can be computed based on the measurement data acquired during the digitization process. At 216, a determination is made as to whether the locations are acceptable. If the locations are not acceptable (e.g., one or more electrode locations being outside of expected locations relative to the other electrodes), the method can return to 204 to repeat the process. In other examples, the process can be implemented two times and if the distance between the measurements for each electrode is more than a predetermined distance (e.g., about 3 mm), the process can require that electrode digitization process be performed an additional time. Where the process is repeated, acceptable location coordinates for each of the electrodes can be averaged to provide corresponding average coordinates for performing source localization. Once it is determined at 216 that the electrode locations are acceptable, the method can proceed to 218 in which the electrode coordinate data is stored for use in source localization, as disclosed herein.

As mentioned above, FIG. 10 depicts an example GUI 250 interface to facilitate digitization of electrode locations. For a given selected electrode configuration, a list of electrodes can be provided at 256, such as can be utilized to indicate which electrode is to be digitized in the map 252. For instance, the electrode that is to be digitized can be highlighted in the list during the process 200 of FIG. 9. Additional instructions regarding each measurement (e.g., confirming instructions and the like) can be provided in the display box 254. Other GUI elements (e.g., buttons) 258 can be provided to activate functions associated with the digitization process, such as to start the process, remove a measurement if a wrong electrode from the identified electrode was incorrectly measured, or to view a report of the digitization process.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 11. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

In this regard, FIG. 11 illustrates one example of a computer system 300 that can be employed to execute one or more embodiments of the invention, such as including acquisition and processing of sensor data, processing of image data, as well as analysis of transformed sensor data and image data associated with the analysis of brain electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the algorithms or methods disclosed herein.

A number of program modules may be stored in drives and RAM 305, including operating system 315, one or more application programs 316, other program modules 317, and program data 318. The application programs and program data can include functions and methods programmed to acquire, process and display electrical data from one or more electrical sensors, such as shown and described herein. The application programs and program data can include functions and methods programmed to perform evaluation and adjustments of data preparation, including parameter adjustment and model selection, such as disclosed herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. For example, while the foregoing source localization is disclosed in the context of localizing a source of brain electrical activity, it could be used for localizing a source of other types of electrical activity, including other parts of the nervous system or muscular system (e.g., muscles such as the heart or others).

As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system to localize a source of electrical activity in a patient's body, the system comprising:
   a non-transitory computer-readable medium to store instructions; and
   a processor to facilitate execution of the instructions to at least:
   preprocess electrical data corresponding to electrical signals acquired from a patient by using a spectral analysis function to determine frequency characteristics of the electrical data and a filter function to filter the electrical data;
   represent the source of electrical activity with an inverse model;
   represent geometry and electrical characteristics of a spatial region of interest in the patient's body based on the inverse model with a forward model;
   compute a location for the source of electrical activity within the spatial region of interest based on the preprocessed electrical data, the inverse model and the forward model;
   evaluate an acceptability of the computed location for the source of electrical activity;
   selectively adjust the filter function based on the frequency characteristics based on the evaluation of the acceptability of the computed location for the source of electrical activity;
   re-compute the location for the source of electrical activity based on the selective adjustment; and
   generate an output comprising the location for the source of electrical activity.

2. The system of claim 1, wherein the processor further facilitates the execution of the instructions to:
   evaluate the acceptability of the computed location for the source of electrical activity based on predefined criteria; and
   perform the selective adjustment automatically based on preprogrammed rules applied to results of the evaluation of the acceptability.

3. The system of claim 2, wherein the selective adjustment further comprises
   adjusting the preprocessing automatically based on the rules; and
   choosing at least one of the inverse model and the forward model based on the rules.

4. The system of claim 2, wherein if the results of the evaluation of the acceptability are unacceptable, the processor further facilitates the execution of the instructions to selectively adjust at least one of the preprocessing component, the inverse model and the forward model for each subsequent location of the source of electrical activity.

5. The system of claim 1, wherein the processor further facilitates the execution of the instructions to:
   estimate relative noise of a plurality of channels that provide the electrical signals;
   remove the electrical data corresponding to noisy channels based on the relative noise;
   selectively control a channel control function to remove the noisy channels from the electrical data based on the acceptability of the computed location for the source of electrical activity; and
   re-compute the location for the source of electrical activity without electrical data corresponding to the noisy channels.

6. The system of claim 1, wherein the processor further facilitates the execution of the instructions to modify the forward model and provide a modified forward model based on the acceptability of the computed location for the source of electrical activity, and re-compute the location for the source of electrical activity based on the modified forward model.

7. The system of claim 1, wherein the processor further facilitates the execution of the instructions to modify the inverse model and provide a modified inverse model based on the acceptability of the computed location for the source of electrical activity, and re-compute the location for the source of electrical activity based on the modified inverse model.

8. The system of claim 1, wherein the processor further facilitates the execution of the instructions to:
   separate artifacts from cerebral electrical activity;
   detect a artifacts separated from the cerebral electrical activity by the component analysis function, the detected artifacts being removed from the electrical signals acquired from the patient to provide artifact-removed electrical data, and
   re-compute the location for the source of electrical activity based on the artifact-removed electrical data.

9. The system of claim 1, wherein the processor further facilitates the execution of the instructions to select an interval corresponding to the electrical activity that is to be localized, and compute the location for the source of electrical activity based on the electrical data residing in the selected interval.

10. The system of claim 1, wherein the output represents the location for the source of electrical activity in a graphical representation of the patient's body.

11. The system of claim 1, wherein the spatial region of interest and the source of electrical activity reside in the patient's brain, and the electrical activity being localized corresponds to a spike in brain electrical activity.

12. A non-transitory computer-readable medium having instructions which, when executed, cause a processor to:
   prepare brain electrical data acquired from a patient and geometry data, wherein the preparation of the brain electrical data includes using a spectral analysis function to determine frequency characteristics of the electrical data and filtering the electrical data acquired for the patient using a filter;
   perform source localization based on the prepared brain electrical data and geometry data to determine a location of a source of electrical activity;
   implement an expert system to evaluate an acceptability of the source localization and to adjust at least one of the preparation of the brain electrical data and the geometry data if the acceptability of the source localization is not within a predetermined acceptability level, wherein the expert system is implemented to adjust at least one parameter of the filter to provide an adjusted filter based on the frequency characteristics based on the acceptability of the source localization of the brain electrical data, and the source localization is re-performed based on modified prepared electrical data that is generated based on filtering using the adjusted filter;

store output data corresponding to the location of the source of electrical activity if the acceptability of the source localization is within the predetermined acceptability level; and generate an output comprising the location for the source of electrical activity.

13. The computer-readable medium of claim 12, wherein the expert system is further programmed to cause noisy channels to be removed from the brain electrical data based on a relative noise analysis of input channels for the brain electrical data, the source localization being re-performed based on the prepared electrical data and geometry data with the noisy channels removed from the brain electrical data.

14. The computer-readable medium of claim 12, wherein the preparation of the brain electrical data employs a forward model, the expert system is further programmed to modify the forward model and provide a modified forward model based on the acceptability of the source localization, the source localization being re-performed based on the modified forward model.

15. The computer-readable medium of claim 12, wherein the preparation of the brain electrical data employs an inverse model, the expert system is further programmed to modify the inverse model and provide a modified inverse model based on the acceptability of the source localization, the source localization being re-performed based on the modified inverse model.

16. The computer-readable medium of claim 12, wherein the geometry data comprises image data for the patient that is registered with electrode location data determined for each of a plurality of electrodes.

17. The computer-readable medium of claim 16, wherein the instructions are further operative to select a temporal interval of electrical signals acquired by the plurality of electrodes, the temporal interval of electrical signals containing electrical activity to be localized, the source localization being performed to compute a location for a source of the electrical activity based on the prepared brain electrical data and geometry data, an inverse model and a forward model.

18. The computer-readable medium of claim 12, wherein the preparation of the brain electrical data further comprises instructions to:

perform component analysis on the brain electrical data to separate artifacts from brain electrical activity; and detect the artifacts separated from the brain electrical activity, the detected artifacts being removed from the brain electrical data acquired from the patient to provide artifact-removed electrical data, the source localization being re-performed based on the artifact-removed electrical data and the geometry data.

* * * * *